(12) United States Patent
Detty et al.

(10) Patent No.: US 7,906,500 B2
(45) Date of Patent: Mar. 15, 2011

(54) CHALCOGENOXANTHYLIUM DYES FOR PURGING BLOOD PATHOGENS AND FOR PHOTODYNAMIC THERAPY

(75) Inventors: Michael R. Detty, Rochester, NY (US); David J. Donnelly, Buffalo, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 0 days.

(21) Appl. No.: 11/195,393

(22) Filed: Aug. 2, 2005

(65) Prior Publication Data

US 2006/0040908 A1     Feb. 23, 2006

Related U.S. Application Data

(60) Provisional application No. 60/598,043, filed on Aug. 2, 2004.

(51) Int. Cl.
*A61K 31/33* (2006.01)
*C07D 345/00* (2006.01)

(52) U.S. Cl. .......................................... 514/183; 540/1

(58) Field of Classification Search ....... 540/1; 514/183
See application file for complete search history.

(56) References Cited

FOREIGN PATENT DOCUMENTS

EP    0 330 444         8/1989
JP    11-279426 A  *   10/1999

OTHER PUBLICATIONS

Detty et al. "Synthesis, properties, and photodynamic properties in vitro of heavy-chalcogen analogues of tetramethylrosamine" Bioorganic & Medicinal Chemistry, Apr. 13, 2004 vol. 12, pp. 2537-2544.*

Ohulchanskyy et al. "Heteroatom Substitution Induced Changes in Excited-State Photophysics and Singlet Oxygen Generation in Chalcogenoxanthylium Dyes: Effect of Sulfur and Selenium Substitutions" Journal of Physical Chemistry B May 1, 2004, vol. 108, pp. 8668-8672.*

Chemical Abstracts Accession No. 1983:135090.*

Detty, M. R., et al., "Synthesis, properties, and photodynamic properties in vitro of heavy-chalcogen analogues of tetramethylrosamine," Bioorganic & Medicinal Chemistry, Apr. 13, 2004, pp. 2537-2544, vol. 12, Elsevier.

Ohulchanskyy, T. Y., et al., "Heteroatom Substitution Induced Changes in Excited-State Photophysics and Singlet Oxygen Generation in Chalcogenoxanthylium Dyes: Effect of Sulfur and Selenium Substitutions," Journal of Physical Chemistry B, May 1, 2004, pp. 8668-8672, vol. 108, American Chemical Society.

Nealy et al; Synthesis of 3,6-Bis(dimethylamino)thio- and Selenoxanthene (1); Monsanto Research Corporation, Boston Laboratory, vol. 3, pp. 228-229, 1966.

* cited by examiner

*Primary Examiner* — Joseph R Kosack
(74) *Attorney, Agent, or Firm* — Hodgson Russ LLP (57) ABSTRACT

Provided are chalcogenoxanthylium compounds which can effectively be used as sensitizers in photodynamic therapy, virucides in photodynamic antimicrobial chemotherapy and reversal agents of Pgp function in cancer cells. Further provided is a general method for the preparation of chalcogenoxanthylium compounds.

9 Claims, 4 Drawing Sheets

Figure 1. Representative examples of rhodamine dyes.

Figure 1

Figure 2. Effect of chalcogen atom substitution on singlet oxygen yields.

Scheme 1

CHALCOGENOXANTHYLIUM DYES FOR PURGING BLOOD PATHOGENS AND FOR PHOTODYNAMIC THERAPY

This application claims priority to U.S. provisional application. 60/598,043, filed on Aug. 2, 2004 the disclosure of which is herein incorporated by reference.

This work was supported by a Grant no. 1-RO1-HL66779-03 from the National Institutes of Health. The Government has certain rights in the invention.

BACKGROUND OF THE INVENTION

Blood is the fluid of life carrying oxygen and nutrient, and when necessary, drugs/pharmaceuticals throughout the body. Following injury and/or during surgery, blood levels or blood components may need to be increased in an individual to sustain life. Blood and blood components taken from donors. However, in the blood of an infected donor, pathogenic (disease-causing) microbes may be present. Screening processes can remove tainted blood from the blood and blood-component supply, but some donors may have been infected only recently and their blood pathogens may not yet be at a high enough concentration to be detected by the screening process. These donors increase the risk of transfusion-transmission of injection.

The risk from pathogen-contaminated blood can be reduced via various sterilization techniques. Photodynamic therapy (PDT) using light, endogenous oxygen, and a photosensitizer has been successfully utilized in the treatment of cancer and the same principles can be applied to the removal of microbes from blood. Irradiation with wavelengths of light absorbed by the photosensitizer produces singlet oxygen through the interaction of the triplet excited state of photosensitizer with ground-state oxygen, which is also a triplet. In the treatment of blood and blood products, photodynamic therapy is known as Photodynamic Antimicrobial Chemotherapy (PACT). However, compounds which are used for the treatment of blood products can damage to the blood cells by causing hemolysis, especially after irradiation.

Figure 1:
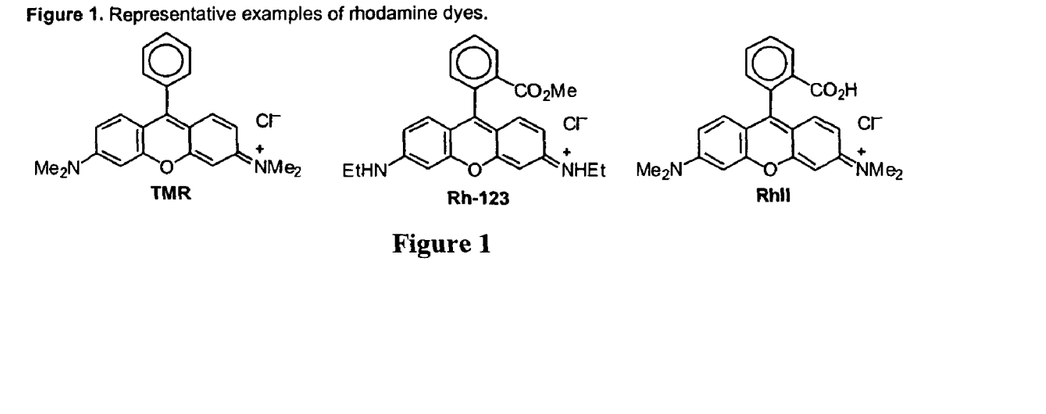
FIG. 1—Representative examples of rhodamine dyes.

Various dyes have been used with mixed success in PDT and PACT. A structure at the heart of many dyes, and indeed, many important chromophores in chemistry and biology, is the xanthylium nucleus. The rhodamine and rosamine dyes (shown in FIG. 1) are representative of the xanthylium class and have been used as laser dyes, fluorescent labels, and fluorescence emission standards where their high fluorescence quantum yields and photostabilities are exploited. [1-5] The rhodamine dyes are also useful fluorescence probes in cell biology studies, showing specific fluorescence staining of mitochondria and other cell organelles. [6,7] The rhodamines have been found to accumulate selectively in carcinoma cells [8-10] and to be toxic to cancer cells both in vitro [10] and in vivo. [11]

One area where the xanthylium dyes have been minimally utilized is photodynamic therapy (PDT), where their tumor specificity might truly be exploited. [12,13] PDT is a treatment for various cancers that utilizes the combination of a tumor-specific photosensitizer, light, and molecular oxygen to induce cellular toxicity, presumably via the generation of singlet oxygen. [12] While rhodamine and rosamine dyes exhibit selective uptake in cancer cells, they are poor producers of excited-state triplets [14] and, consequently, of singlet oxygen. The poor triplet production limits the use of rhodamine and rosamine dyes as photosensitizers PDT. Furthermore, the rhodamines and rosamines absorb light of wavelengths too short for effective penetration in tissue. [12]

Heavy-atom effects in brominated rhodamine dyes give increased triplet yields and quantum yields for the generation of singlet oxygen [$\phi(^1O_2)$] [15-17] relative to unmodified rhodamines. [18] However, wavelengths of absorption are little changed relative to their light-atom counterparts. The brominated analogues still target the mitochondria and have increased phototoxicity toward cancer cells. [17] Accordingly, there is a need in the areas of PDT and PACT to identify new compounds useful in these methodologies.

One compound which has been used in photodynamic therapy studies is tetramethyl rosamine (TMR-O). While TMR-O has promise in that it has been shown to be transported into the cell cytoplasm, its ultimate ability to be effective is in doubt; as with other rosamine dyes, upon irradiation, TMR-O exhibits a high degree of fluorescence at the expense of singlet oxygen production, the species which damages tumor cells such that they die rather than replicate.

On yet another front in the treatment of cancer, multidrug resistance (MDR) of tumor cells, mediated by the plasma membrane protein P-glycoprotein (Pgp), is a major concern for treatment of primary, metastatic and recurrent cancer. [26-28] Pgp pumps a variety chemicals and chemotherapeutic agents from tumor cells, resulting in treatment failures. [26, 29-31] Tumor cell resistance to a wide assortment of chemotherapeutic agents can arise from exposure to a single drug making subsequent treatments ineffective. [26-27]

The mechanism by which Pgp overexpression is induced during exposure to chemotherapeutics or chemical agents is not fully understood, and may occur at the transcriptional level by mechanisms such as gene amplification, gene rearrangement, DNA methylation, promoter mutation or chromatin modification. [32, 33] With any one of these factors, transcription is the key for induction of Pgp and in some cases this could be a rapid response to intra/extracellular stimuli. [32] Development of therapeutic interventions at the transcriptional level could be advantageous. Currently, the most direct approach to inhibiting Pgp function in cancer is at the level of binding and/or the inhibition of ATP hydrolysis that Pgp is dependent upon for drug efflux from cells.

Many MDR reversal agents, including verapamil, cyclosporin A, and PSC833, have been examined to counteract the mechanisms of drug resistance. [34-36] However, these compounds have significant drawbacks, such as alterations in cell metabolism and their toxicity toward normal tissues. The therapeutic window for these compounds is severely restricted because the dose necessary for effective inhibition of Pgp, in many cases, exceeds the minimal toxic concentration in normal tissue. [26, 37,38] Ideally, Pgp modulators would be administered in combination with chemotherapeutic agent(s) to increase anti-cancer drug uptake, retention and effectiveness. However, concomitant administration of high doses of modulators and therapeutic doses of anti-cancer agents have resulted in unacceptable toxicity requiring chemotherapeutic dose reduction and ineffective treatment. [38]

One source of Pgp inhibitors might be derived from the cationic rhodamine dyes, such as rhodamine 123 (Rh123) and tetramethylrosamine (TMR-O), both structure given directly below. [39-41] These dyes are transport substrates for Pgp and have been used as fluorescent markers to determine the efficacy of Pgp modulators. [41,42] However, Rh123 and TMR-O do not inhibit Pgp function. [41,43]

While TMR-O is a Pgp substrate, it has not been completely clear why this is so. Furthermore, variations of TMR-O, such as its sulfur and selenium analogs, are not readily available, as sulfur and selenium analogs of xanthylium compounds (chalcogenoxanthylium compounds) are more difficult to prepare than xanthylium compounds. In particular, the selenium analogs are difficult to prepare with available methods.

SUMMARY OF THE INVENTION

Figure 4:
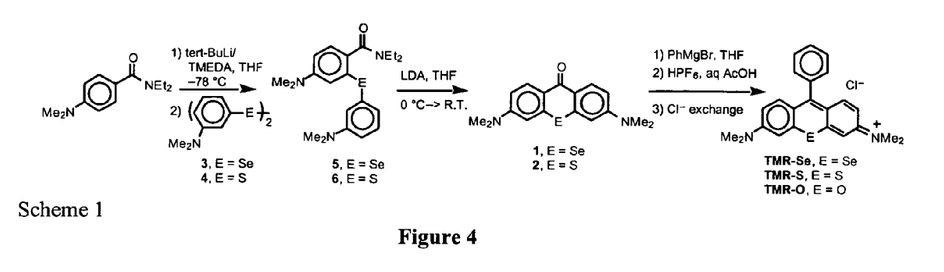
FIG. 4—Synthesis schematic for chalcogenoxanthylium compounds.
Figure 5:
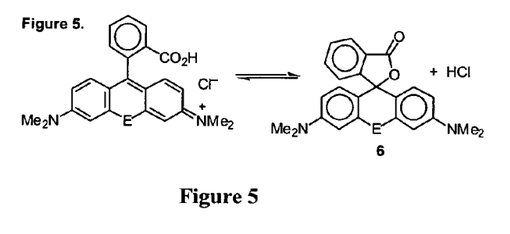
FIG. 5—General method for the preparation of chalcogenoxanthylium compounds.

Provided are chalcogenoxanthylium compounds, i.e., selenium and sulfur analogs of xanthylium compounds. A method for their preparation from available or easily prepared precursors via directed metallation reactions is also provided (FIG. 4). Further provided are selenium and sulfur analogs of TMR-O, as well as other chalcogenoxanthylium compounds, which have high efficiency in producing singlet oxygen and can be used as sensitizing agents in PDT and PACT. Further provided is a method for their synthesis. Further provided are compounds, TMR-Se and TMR-S having the ability to inhibit Pgp function in cancer cells.

DETAILED DESCRIPTION OF THE INVENTION

Figure 2:
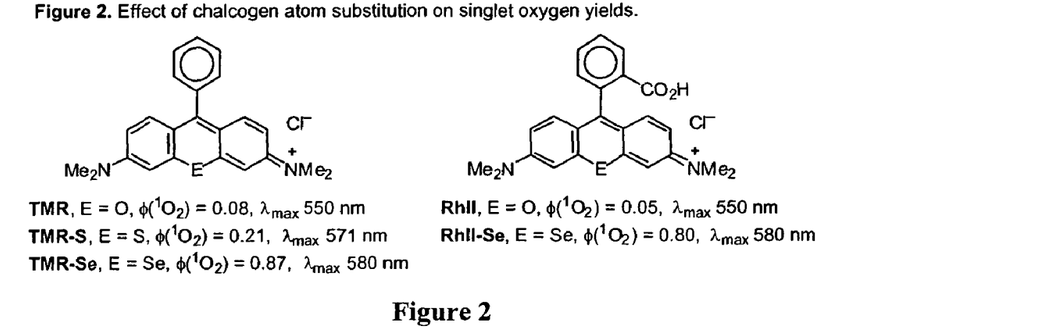
FIG. 2—Effect of chalcogen atom substitution on singlet oxygen yield.
Figure 3:
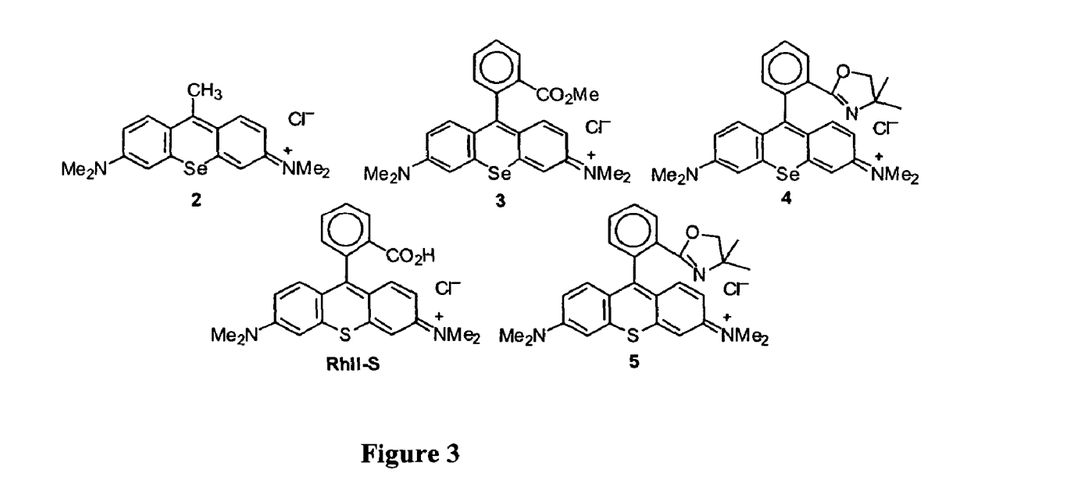
FIG. 3—Examples of chalcogenoxanthylium compounds.

Chalcogenoxanthylium compounds have been found to generally demonstrate greater formation of singlet oxygen in response to photostimulation than their oxygen counterparts. Chalcogenoxanthylium compounds which are amino substituted at the 2 and 7 positions, and particularly those which have an aryl group as a substituent in the 9-position have shown the potential for a high degree of virucidal activity. Specifically, TMR-Se and TMR-S have demonstrated high production of singlet oxygen in response to photostimulation in in vitro studies. Not only does substitution of sulfur or selenium for oxygen in the xanthylium core give dramatic increases in the production of $^1O_2$ in the photostimulated compound, but this substitution also gives longer wavelengths of absorption and emission and provides highly effective photosensitizers for PACT. Some compounds of the present invention are illustrated in FIG. 2 and also include compounds 3, 4, RhII-S and 5 in FIG. 3.

Thus, the present invention provides a method for reducing blood or blood product pathogens by incubating blood with a pathogen-purging amount of one or more compounds of the present invention and exposing the blood or blood product to radiation, preferably white light, which excites the dye molecules to their first electronically excited state. The term "blood products" as used herein refers to whole blood, red blood cells, white blood cells, platelets or other blood fractions and products which are derived from or fabricated from blood. The term "blood pathogens" as used herein means viruses and/or bacteria.

For example, TMR-Se, when incubated with red blood cells, was observed to have extremely high extracellular virucidal activity. TMR-S could also inactivate extracellular virus, but generally required higher concentrations and a higher degree of light exposure than TMR-Se.

Additionally some chalcogenoxanthylium compounds, such as TMR-Se and RhII-Se were able to perform as virucides in red blood cell solutions with little apparent hemolysis following photoactivation of the dye. This lack of hemolysis persists even during storage following photoexcitation of the dye. The high extracellular and intracellular inactivation levels and low hemolysis during storage with RhII-Se is unexpected. In a study of over fifty photosensitizers, it was observed that none could inactivate virus to this degree without significant hemolysis during storage.

Thus, it is believed that chalcogenoxanthylium compounds, especially those having an aromatic substituent at the 9-position, can be used as potent photosensitizers for PDT.

Furthermore, experiments with chalcogenoxanthylium compounds strongly suggest that TMR-Se and TMR-S are transport substrates for Pgp, similarly to TMR-O, and may act as reversal agents of Pgp function.

TMR-S and TMR-Se and light can increase the intracellular accumulation of the Pgp substrate CAM into chemoresistant CR1R12 cells. Initial experiments demonstrate that highly expressing Pgp cells can be altered by these tetramethylrosamine analogues to take in 2 times more Pgp substrate than cells not exposed to the dyes and light. [44] TMR-S and TMR-Se are phototoxic to chemo-resistant CR1R12 cells when a Pgp modulator is present indicating that uptake ensues and that the dyes are able to reach and cause damage to a critical intracellular sites during irradiation.

The present invention describes dyes having the following formula:

Formula I

Wherein R is an alkyl group of 1-8 carbons, aryl, substituted aryl, heteroaryl, substituted heteroaryl group and E is S or Se. The aryl group may be mono-, di-, or tri-substituted with substituents at the ortho, meta, or para positions. Useful substituents include, but are not limited to, —$CO_2Me$, —$CO_2H$, —$NMe_2$ and other dialkylamino (each alkyl group independently having 1-8 carbons), —NHEt and other alkylamino (of 1-8 carbons), —$NH_2$, —Me and other alkyl (of 1-8 carbons), —OMe and other alkoxy (of 1-8 carbons), and various heterocyclic groups such as 1,3-oxazole, 1,3-diazole, 4,5-dihydro-1,3-oxazole, and 4,5-dihydro-1,3-thiazole.

$A^-$ is an anionic group selected from $Cl^-$ and other halides, tosylate and other sulfonates, acetate and other carboxylates, hexafluorophosphate, tetrafluoroborate, and the like;

wherein $R_1'$, $R_2'$, $R_1''$ and $R_2''$ of the amino substituents at the 2- and 7-positions of the chalcogenoxanthylium core may be the same or different and may be selected from hydrogen and branched or straight alkyl groups having eight or fewer carbon atoms. R1' and R2' and/or R1" and R2" may be connected such that, together with the attached nitrogen, a 3, 4, 5, 6 or 7 member ring structure, optionally bearing alkyl substituents, is formed. For example, the ring structure may be a substituted piperidine.

The compounds may bear W, X, Y and Z substituents which are, independently, hydrogen or $C_1$ through $C_8$ alkyl join the nitrogen substituents such that a single or double ring structure is formed on either or both end rings of the molecule. The rings which comprise the nitrogen substituents and substituents W, X, Y and Z may be 5, 6 or 7 member rings, for example. The structure below illustrates a compound having a two ring structure on one xanthylium end ring of the compound.

The substitution on the aryl ring may also be a ring structure such as in compounds having the following formula:

The compounds of the present invention also include spirolactone compounds having the following structure, in which E is preferably Se:

Such spirolactone compounds generally exist in equilibrium with their ring-opened form, in relative proportions which depend upon the pH of their environment, with the proportion of spirolactone increasing with pH.

The present invention also provides a method for the synthesis of sulfur and selenium analogues of xanthylium compounds, i.e., compounds in which the oxygen in the xanthylium backbone is replaced by sulfur or selenium. Some compounds of the present invention are illustrated below, as well as in FIG. 2. In particular the sulfur and selenium analogs of tetramethylrosamine (TMR-S and TMR-Se, respectively) can be effectively synthesized according to the method of the present invention.

In particular, the compounds of the present invention e.g., chalcogenoxanthylium compounds, including the thio and seleno analogues of tetramethylrosamine, are prepared by the directed-metallation/cyclization of the corresponding N,N-diethyl 2-(3-dimethylaminophenylchalcogeno)-4-dimethylaminobenzamide to the 2,7-bis-(N,N-dimethylamino)-9H-chalcogenoxanthen-9-one followed by the addition of phenylmagnesium bromide, dehydration and ion exchange to the chloride salt. The thio and seleno tetramethylrosamines had longer wavelengths of absorption and higher quantum yields for the generation of singlet oxygen than tetramethylrosamine. Both the thio and seleno analogues of tetramethylrosamine can be used for PACT.

A general method for the preparation of the compounds disclosed above is outlined below, and comprises the following steps:

1) Providing a compound (1) of the following structure:

(1)

I)
i) Y and Z are hydrogen;
ii) $R_1'$ and $R_2'$, are independently hydrogen or $C_1$ through $C_8$ branched or unbranched alkyl groups and, optionally, $R_1'$ and $R_2'$ are alkyl groups connected such that they comprise a three, four, five, six or seven-membered ring:

which, if desired, can bear substituents such as, for example, alkyl or aryl groups; or II)
i) Y and Z are independently hydrogen or $C_1$ through $C_8$ alkyl and $R_1$ and $R_2$ are independently hydrogen or $C_1$ through $C_8$ alkyl; wherein $R_1$ and Y are connected such that they comprise a five, six or seven-membered ring:

and/or $R_2'$ and Z are connected such that they comprise a five-, six- or seven-membered ring:

Compounds of the above structure (1) can be obtained commercially or prepared from appropriately substituted carboxylic acid derivatives by first forming the corresponding acid chloride with oxallyl chloride or thionyl chloride and then treating with diethylamine. It is not essential that the substituents on the amide nitrogen be ethyl groups, and other alkyl groups, such as branched and unbranched alkyl groups, such as those comprising eight or fewer carbons can be used instead of ethyl groups.

2) Forming a reaction mixture comprising compound (1), N,N,N,N-tetramethylethylenediamine (TMEDA), sec- or tert-butyl lithium and a solvent whereby said compound (1) is lithiated at the 2 position. The reaction mixture is generally formed by first combining compound (1) with TMEDA in a solvent, followed by the addition of the butyl lithium component. The butyl lithium component is preferably added in a controlled manner, such as by dropwise addition to the solution containing the other reactants. A range of solvents can be used, including for example such common solvents as Tetrahydrofuran (THF), ether, and dimethoxyethane. THF is preferred.

3) Adding a compound (2) of the following structure:

(2)

to the reaction mixture such that a compound (3), of the following structure is formed:

(3)

wherein E is S or Se, and

I)
i) W and X are hydrogen;
ii) $R_1''$ and $R_2''$ are independently hydrogen, $C_1$ through $C_8$ branched or unbranched alkyl and, optionally, $R_1''$ and $R_2''$ are alkyl groups connected such that they comprise a three, four, five, six or seven-membered ring:

which, if desired, can bear substituents such as alkyl or aryl groups; or

II)
i) W and X are independently hydrogen or $C_1$ through $C_8$ alkyl;
ii) $R_1''$ and/or $R_2''$ are independently hydrogen or $C_1$ through $C_8$ alkyl;
and wherein $R_1''$ and W are connected such that they comprise a five, six or seven-membered ring:

and/or wherein $R_2''$ and X are connected such that they comprise a five-, six- or seven-membered ring:

As with $R_1'$ and $R_2'$, $R_1''$ and $R_2''$ are independently hydrogen or straight or branched alkyl groups, preferably having 8 or fewer carbon atoms.

Compound (2), referred to herein as a "dichalcogenide" compound, can be prepared by the use of a 3-Bromoaniline (optionally N-substituted with one or two alkyl groups, branched or straight, each having 8 or fewer carbons), magnesium, and elemental sulfur or selenium, such as sulfur powder, selenium metal, whole or crushed selenium shot, selenium shavings, etc., to form a 3-chalcogenolated aniline compound. The bromoaniline compound and magnesium are first reacted to form a Grignard reagent. The Grignard reagent is then reacted with the elemental sulfur or selenium. Preferably, the 3-bromoaniline compound, the magnesium and a solvent are combined and refluxed for a time, preferably in the range of 0.5 h to 4 h, after which the mixture is cooled, preferably to room temperature. Elemental sulfur or selenium is then added to the solution containing the Grignard reagent. The mixture is again refluxed for a time in the range of from 0.5 h to 4 h, and cooled, preferably to about room temperature or below, such as by allowing it to stand for a time. It is then diluted with water and cooled further, both of which can be accomplished simultaneously by pouring the mixture over ice. An acid such as HCl is added to the mixture to give a 3-chalcogenolated compound, after which the 3-chalcogenolated compound is oxidized to the dichalcogenide compound. The oxidation is preferably accomplished by contacting the dichalcogenolated compound with a mild oxidant such as air or an alkylated or arylated selenoxide or telluroxide, such as dihexyl telluroxide. It is preferred to maintain a temperature in the range of 0 to −100° C. during the addition of the butyl lithium and the dichalcogenide.

The dichalcogenide compound is added to the reaction mixture, preferably in a controlled manner, such as by dropwise addition while dissolved in a suitable solvent, such as THF. It is preferred that the dichalcogenide be added after the butyl lithium. It is also preferred to reflux for a time greater than 0.5 h after the addition of the butyl lithium compound and before dichalcogenide addition.

4) Contacting said compound (3) with lithium diisopropylamide (LDA) to form a compound (4) of the following structure:

(4)

Compound (3) is contacted with LDA, preferably by dissolving compound (3) in a solvent to form a first solution, and adding LDA, preferably solvated as a second solution, and stirring the combined for a time in the range of 0.1 to 2 hours, followed by quenching with a quencher, preferably a saturated ammonium chloride solution.

5) converting compound (4) to a compound (5) of the following structure:

(5)

wherein R is an alkyl group of 1-8 carbons, aryl, substituted aryl, heteroaryl, or substituted heteroaryl group and E is S or Se. The aryl group may be mono-, di-, or tri-substituted with substituents at the ortho, meta, or para positions. Useful substituents include, but are not limited to, —CO$_2$Me, —CO$_2$H, —NMe$_2$ and other dialkylamino (each alkyl group independently having 8 or fewer carbons), —NHEt and other alkylamino (of 1-8 carbons), —NH$_2$, —Me and other alkyl (of 1-8 carbons), —OMe and other alkoxy (of 1-8 carbons), and various heterocyclic groups such as 1,3-oxazole, 1,3-diazole, 4,5-dihydro-1,3-oxazole, and 4,5-dihydro-1,3-thiazole.

A$^-$ is an anionic group such as Cl$^-$ or other halides, tosylate or other sulfonates, acetate or other carboxylates, hexafluorophosphate, tetrafluoroborate, and the like.

It may be convenient to sequentially perform two or more of the preceding steps in the "same pot." However, it is preferred that resulting compounds (1), (2), (3) and (4) be purified to some degree before their use in a subsequent step, which may be accomplished by methods known in the art.

The preferred method of conversion of a compound (4) to compound (5) depends upon the R group desired in the end product. However, the conversion can generally be accomplished by methods including the use of Grignard-type reagents or organolithium reagents. For example alkyl magnesium bromides and/or alkyl lithiums and phenyl magnesium bromides and/or aryl lithiums can be used to add an alkyl or a phenyl group, respectively, at the ketone carbon chain of compound (4). Substituted aryl groups or heteroaryl groups can also be added by the use of Grignard-type reagents in appropriate solvents. As is well known in the art, the treatment of a ketone compound with either a Grignard reagent or an organolithium reagent, followed by acidification of the solution results in the formation of an alcohol compound. In order to prepare a chalcogenoxanthylium compound of Formula I, it is necessary to convert the alcohol to a chalcogenoxanthylium salt. Counter anions include halides, such as, for example, Cl$^-$; sulfonates such as, for example, tosylate; carboxylates, such as, for example acetate; hexafluorophosphate; tetrafluoroborate; and the like. Salt formation can be accomplished by the addition of the acid of the desired counter anion. For example, the addition of hydrochloric acid or hexafluorophosphoric acid to the solution following Grignard treatment will give the chloride and hexafluorophosphate salts, respectively. The acid is preferably added to the solution in a controlled manner, such as, for example, dropwise addition. The chalcogenoxanthylium chloride or hexafluorophosphate salt can be precipitated from the solution by cooling the solution to a temperature in the range of −50° C. to 0° C.

Further changing of the anion identity, such as conversion of hexafluorophosphate salt to a chloride salt can be accomplished by methods known in the art, such as, for example, ion exchange resins and the like. The foregoing method is illustrated in FIG. 4.

The following examples describe the synthesis of the compounds of the present invention.

General experimental: Solvents and reagents were used as received from Sigma-Aldrich Chemical Co (St. Louis, Mo.) unless otherwise noted. Tetramethylrosamine (TMR-O) was purchased from Molecular Probes, Inc. Cell culture media and antibiotics were obtained from Grand Island Biological (Grand Island, N.Y.). Fetal bovine serum (FBS) was purchased from Atlanta Biologicals (Atlanta, Ga.). Concentration in vacuo was performed on a Büchi rotary evaporator. Chalcogenoxanthones 1 and 2 were prepared as shown in Scheme 1 in FIG. 4 by a method described herein. NMR spectra were recorded on a Varian Inova 500 instrument with residual solvent signal as internal standard. UV-visible-near-IR spectra were recorded on a Perkin-Elmer Lambda 12 spectrophotometer equipped with a circulating constant-temperature bath for the sample chambers. Elemental analyses were conducted by Atlantic Microlabs, Inc.

Example 1

Preparation of Di-3-(N,N-dimethylamino)phenyl Disulfide (4): 3-Bromo-N,N-dimethylaniline (1.0 g, 5.0 mmol)

was added to a stirred mixture of Mg turnings (0.243 g, 10.0 mmol) in 10 mL of anhydrous THF. The resulting mixture was heated reflux for 2 h and then cooled to ambient temperature. Sulfur powder (0.39 g, 5.0 mmol) was added and the resulting mixture was heated at reflux for 2 h. The reaction mixture was cooled to ambient temperature and then poured over 6 g of ice. Ten mL of 5% HCl was added and the resulting mixture was filtered through a pad of Celite. The crude thiol was oxidized via the addition of 0.074 g (0.24 mmol) of dihexyltelluride and 10 mL of 30% $H_2O_2$. [23] After stirring for 1 h, the reaction mixture was poured into 50 mL of water and the crude product was extracted with ether (3×25 mL). The combined organic extracts were washed with brine, dried over $MgSO_4$, and concentrated. The crude oil was purified via chromatography on $SiO_2$ eluted with 10% cyclohexane/$CH_2Cl_2$ to give 0.79 g (52%) of the disulfide 4 as a white powder, mp 91-92° C.: $^1H$ NMR ($CD_2Cl_2$) δ 7.81 (d, 2H, J=6.7 Hz), 7.21 (d×d, 1H, J=2.0, 6.7 Hz), 3.35 (s, 12H); HRMS (EI), m/z 304.1065 (Calcd for $C_{16}H_{20}N_2S_2$: 304.1068). Anal. Calcd for $C_{16}H_{20}N_2S_2$: C, 63.12; H, 6.62; N, 9.20. Found: C, 63.08; H, 6.62; N, 9.23.

Example 2

Preparation of N,N-Diethyl 4-N,N-Dimethylamino-2-[3-(N,N-dimethylamino)-phenylthio]benzamide (6): sec-Butyllithium (1.3 M in cyclohexane, 2.7 mL, 3.6 mmol) was added dropwise to a stirred solution of N,N-diethyl 4-N,N-dimethylamino benzamide (0.79 g, 3.6 mmol) and N,N,N,N-tetramethylethylenediamine (TMEDA, 0.42 g, 3.6 mmol) in 25 mL of anhydrous THF at −78° C. After 1 h at −78° C., disulfide 4 (1.43 g, 3.6 mmol) in 5 mL THF was added dropwise. After 0.5 h at −78° C., the reaction mixture was warmed to ambient temperature. Ten mL of saturated $NH_4Cl$ was added and the products were extracted with $CH_2Cl_2$ (3×30 mL). The combined organic extracts were washed with brine, dried over $MgSO_4$ and concentrated. The crude product was purified via chromatography on $SiO_2$ eluted with 20% ether/$CH_2Cl_2$ to give 0.25 g (51%) of 6 as a pale yellow oil: $^1H$ NMR ($CD_2Cl_2$) δ 7.17 (t, 1H, J=8 Hz), 7.08 (d, 1H, J=8.5 Hz), 6.81 (t, 2H, H, J=8 Hz), 6.63 (d×d, 1H, J=2, 8.5 Hz), 6.60 (d, 1H, J=2 Hz), 6.58 (d×d, 1H, J=2, 8.5 Hz); 3.50 (exchange broadened s, 4H), 3.18 (s, 6H), 2.86 (exchange broadened s, 6H); $^{13}C$ NMR ($CD_2Cl_2$) δ 169.5, 151.4, 151.0, 135.7, 133.8, 129.7, 127.5, 127.2, 119.7, 115.6, 115.0, 111.6, 111.0, 43.2 (br), 40.5, 40.2, 14.2 (br); IR (film, NaCl) 1621, 1594 cm$^{-1}$; HRMS (ES) m/z 372.2109 (Calcd for $C_{21}H_{30}N_3OS$+H: 372.2104).

Example 3

Preparation of 2,7-Bis-N,N-(dimethylamino)thioxanthen-9-one (2): To a solution of 6 (0.52 g, 1.5 mmol) in 10 mL of THF at 25° C. was added LDA (1.0 M in hexanes, 3.6 mL, 3.6 mmol). The resulting mixture was stirred at ambient temperature for 15 h and was quenched by the addition of 20 mL of saturated $NH_4Cl$. The products were extracted with $CH_2Cl_2$ (3×10 mL) and the combined organic extracts were washed with brine, dried over $Na_2SO_4$, and concentrated. The products were purified via chromatography on $SiO_2$ eluted with 10% ether/$CH_2Cl_2$ to give 0.37 g (70%) of recovered 6 and 0.52 g (13%) of 2 as a yellow powder, mp 260-261° C.: $^1H$ NMR [500 MHz, $CD_2Cl_2$] δ 8.33 (d, 2H, J=9.2 Hz), 6.80 (d×d, 2H, J=2.1, 9.2 Hz), 6.77 (d, 2H, J=2.1 Hz), 3.07 (s, 12H); $^3C$ NMR ($CD_2Cl_2$) 177.2; 151.7, 138.6, 130.2, 118.5, 110.9, 104.8, 39.6; IR (KBr) 1592 cm$^{-1}$; HRMS (ES) m/z 299.1217 (Calcd for $C_{17}H_{18}ON_2S$+H: 299.1213).

Example 4

Preparation of 2,7-Bis-N,N-dimethylamino-9-phenylselenoxanthylium Chloride (TMR-Se): A solution of 2,7-bis-N,N-dimethylamino-9H-selenoxanthen-9-one (1, 0.070 g, 0.20 mmol) in THF (3 mL) was added dropwise to a solution of phenylmagnesium bromide (1.0 mL of a 1.0 M solution in THF, 1.0 mmol) in THF (2 mL) heated to reflux. After addition was complete, the resulting solution was heated at reflux for an additional 0.5. The reaction mixture was then cooled to ambient temperature and poured into acetic acid (3.0 mL). Hexafluorophosphoric acid (60% weight solution in water) was added dropwise until the initial deep blue solution turned reddish yellow. Water (50 mL) was added and the resulting mixture was cooled at −10° C. precipitating the selenoxanthylium hexafluorophosphate salt. The dye was collected by filtration and the solid was washed with water (2×5 mL) and diethyl ether (2×5 mL). The crude product was recrystallized by dissolving the solid in 2 mL of hot $CH_3CN$, cooling to ambient temperature, slowly adding 2 mL of ether, and chilling. The recrystallized product was collected by filtration, washed with ether (2×5 mL), and dried to give 0.109 g (98%) of the hexafluorophosphate salt as a dark green solid: mp>260° C.; $^1H$ NMR [500 MHz, $CD_2Cl_2$] δ 7.62 (m, 3H) 7.44 (d, 2H, J=9.8 Hz), 7.30 (m, 2H), 7.27 (d, 2H, J=2.5 Hz), 6.83 (d×d, 2H, J=2.5, 9.8 Hz), 3.25 (s, 12H); $^{13}C$ NMR [500 MHz, $CD_2Cl_2$] δ 161.3, 152.6, 146.1, 138.1, 136.9, 128.9, 128.8, 128.3, 119.6, 114.4, 109.2, 40.4; $\lambda_{max}$ ($CH_2Cl_2$) 582 nm (ε=6.9×10$^4$ M$^{-1}$ cm$^{-1}$); HRMS (ES) m/z 407.1038 (Calcd for $C_{23}H_{23}N_2^{80}Se$: 407.1026). Anal. Calcd for $C_{23}H_{23}F_6N_2OPSe$: C, 50.10; H, 4.20; N, 5.08. Found: C, 50.20; H, 4.32; N, 4.96.

The hexafluorophosphate salt (0.109 g, 0.068 mmol) was dissolved in 20 mL of acetonitrile and 0.500 g of Amberlite IRA-400 Chloride ion exchange resin was added. The resulting mixture was stirred 0.5 h, the exchange resin was removed via filtration, and the process was repeated with two additional 0.500-g aliquots of the ion exchange resin. Following the final ion exchange, the filtrate was concentrated and the solid residue was recrystallized from acetonitrile and a small amount of diethyl ether to give 0.081 g (75%) of 2,7-bis-N,N-dimethylamino-9-phenylselenoxanthylium chloride (TMR-Se) as a dark purple solid: mp>260° C.; $^1H$ NMR [500 MHz, $CD_2Cl_2$] δ 7.63 (m, 3H), 7.44 (d, 2H, J=6.1), 7.30 (d×d, 2H, J=1.8, 7.3 Hz), 7.28 (d×d, 2H, J=2.1, 7.3 Hz), 6.83 (d×d, 2H, J=2.1, 9.1 Hz), 3.25 (s, 12H); $\lambda_{max}$ ($H_2O$) 580 nm (ε=5.9× 10$^4$ M$^{-1}$ cm$^{-1}$); HRMS (ES) m/z 407.1038 (Calcd for $C_{23}H_{23}N_2^{80}Se$: 407.1026). Anal. Calcd for $C_{23}H_{23}ClN_2OSe$: C, 62.52; H, 5.25; N, 6.34. Found: C, 62.46; H, 5.08; N, 6.28.

Example 5

Preparation of 2,7-Bis-N,N-dimethylamino-9-phenylthioxanthylium Chloride (TMR-S): A solution of 2,7-bis-N,N-dimethylamino-9H-thioxanthen-9-one (2, 0.050 g, 0.17 mmol) in THF (3 mL) was treated with phenylmagnesium bromide (1.0 mL of a 1.0 M solution in THF, 1.0 mmol) in THF (2 mL) as described for TMR-Se. Workup and recrystallization gave 0.078 g (71%) of 2,7-bis-N,N-dimethylamino-9-phenylthioxanthylium hexafluorophosphate: mp>260° C.; $^1H$ NMR [500 MHz, $CD_2Cl_2$] δ 7.68 (m, 3H), 7.47 (d, 2 H, J=9.8 Hz), 7.37 (m, 2H), 7.14 (d, 2H, J=2.4 Hz), 6.95 (d×d, 2H, J=2.4, 9.8 Hz), 3.31 (s, 12H); $^{13}C$ NMR [500 MHz, $CD_2Cl_2$] δ 153.5, 144.4, 136.5, 135.4, 129.5, 129.2, 128.7, 119.2, 115.1, 114.2, 105.4, 40.5; $\lambda_{max}$ ($CH_2Cl_2$) 571 nm (ε=5.0×10$^4$ M$^{-1}$ cm$^{-1}$); HRMS (ESI) m/z 359.1580 (Calcd for $C_{23}H_{23}N_2S$: 359.1582). Anal. Calcd for $C_{23}H_{23}F_6N_2OPS$: C, 54.76; H, 4.60; N, 5.55. Found: C, 54.75; H, 4.75; N, 5.24.

The hexafluorophosphate salt (0.045 g, 0.068 mmol) was treated with Amberlite IRA-400 Chloride ion exchange resin as described for the preparation of TMR-Se to give 0.026 g (78%) of 2,7-bis-N,N-dimethylamino-9-phenylthioxanthylium chloride (TMR-S) as a dark green, crystalline solid: mp>260° C.; $^1H$ NMR [500 MHz, $CD_2Cl_2$] δ 7.67 (m, 3H), 7.46 (d, 2H, J=9.1 Hz), 7.36 (m, 2H), 7.14 (d, 2H, J=2.5 Hz), 6.95 (dxd, 2H, J=2.5, 9.1 Hz), 3.31 (s, 12H); $\lambda_{max}$ (H$_2$O) 570 nm ($\epsilon$=4.0×10$^4$ M$^{-1}$ cm$^{-1}$); HRMS (ESI), m/z 359.1579 (Calcd for C$_{23}$H$_{23}$N$_2$S: 359.1582). Anal. Calcd for C$_{23}$H$_{23}$ClN$_2$OS: C, 69.94; H, 5.87; N, 7.07. Found: C, 70.03; H, 5.75; N, 7.05.

Example 6

Synthesis of 2,7-bis-N,N-dimethylamino-9H-thioxanthen-4-one (2): The synthesis of 2,7-bis-N,N-dimethylamino-9H-selenoxanthen-4-one (1) (numbers in this example refer to FIG. 4) from acyclic precursors via directed metallation reactions is shown in Scheme 1 (FIG. 4).[19] The same approach was used for the synthesis of 2,7-bis-N,N-dimethylamino-9H-thioxanthen-4-one (2). Lithiation of N,N-diethyl 4-dimethylaminobenzamide with tert-BuLi in the presence of N,N,N',N'-tetramethylethylenediamine (TMEDA) followed by the addition of di-(3-dimethylamino) phenyl diselenide (3) or disulfide (4) gave 2-arylselenobenzamide 5 or 2-arylthiobenzamide 6 in 57 and 51% isolated yields, respectively. Cyclization of 5 and 6 with two equivalents of lithium diisopropylamide (LDA) gave selenoxanthenone 1 in 23% yield and thioxanthenone 2 in 13% yield, respectively, with 70% recovered starting material in each case. The starting material could be recycled to give more 1 and 2. Use of larger excesses of LDA gave up to 30% yields of 1 and 2, but no starting material was recovered under these conditions.

The addition of phenylmagnesium bromide to chalcogenoxanthen-9-ones 1 and 2 followed by dehydration with HPF$_6$ gave 2,7-bis-N,N-dimethylamino-9-phenylselenoxanthylium and 2,7-bis-N,N-dimethylamino-9-phenylthioxanthylium hexafluorophosphates in 98 and 71% isolated yields, respectively. Anion exchange with Amberlite IRA-400 chloride exchange resin gave the corresponding chloride salts TMR-Se, and TMR-S in 78 and 75% isolated yields, respectively.

The following example demonstrates that the use of sulfur and selenium analogs of anthylium-type compounds results in increased production of singlet oxygen with respect to TMR-O. Increased singlet oxygen concentration corresponds to greater efficacy of the xanthylium compound as a PDT and PACT agent. In addition, the cyclic voltammetry results show that TMR-S and TMR-Se are more difficult to reduce than AA1, a compound which has been successfully used in PDT. This result indicates that reduction (inactivation) of TMR-S and TMR-Se in the mitochondria is unlikely to occur to such a degree as to compromise the usefulness of TMR-S and TMR-Se as PDT and PACT agents.

Example 7

Experimental

Quantum Yield Determinations for the Generation of Singlet Oxygen: The quantum yields for singlet-oxygen generation with chalcogenoxanthylium dyes TMR-O, TMR-S were measured by direct methods in MeOH.[24] A SPEX 270M spectrometer (Jobin Yvon) equipped with InGaAs photodetector (Electro-Optical Systems Inc., USA) was used for recording singlet-oxygen emission spectra. A diode pumped solid-state laser (Millenia X, Spectra-Physics) at 532 nm was the excitation source. The sample solution in a quartz cuvette was placed directly in front of the entrance slit of the spectrometer and the emission signal was collected at 90-degrees relative to the exciting laser beam. An additional longpass filter (850LP) was used to attenuate the excitation laser and the fluorescence from the photo sensitizer.

Fluorescence Quantum Yields and Radiative Lifetimes: Fluorescence quantum yields ($\phi_F$) and radiative lifetimes ($\tau_{rad}$) were determined using techniques and equipment described in Baker, G. A.; Bright, F. V.; Detty, M. R.; Pandey, S.; Stilts, C. E.; Yao, H. R. J. *Porphyrins Phthalocyanines* 2000, 4, 669. [25] The results are shown in Table I.

Measurement of Reduction Potential: A BAS 100 potentiostat/galvanostat and programmer were used for the electrochemical measurements. The working electrode for cyclic voltammetry was a platinum disk electrode (1-mm diameter) obtained from Princeton Applied Research. The auxiliary and reference electrodes were silver wires. The reference for cyclic voltammetry was the ferrocene/ferrrocinium couple at +0.40 V at a scan rate of 0.1 V s$^{-1}$. All samples were run in J. T. Baker HPLC-grade dichloromethane that had been stored over 3A molecular sieves and freshly distilled prior to use. Tetrabutylammonium fluoroborate (Sigma-Aldrich) was recrystallized from EtOAc-ether and then dried overnight at 80° C. under vacuum before it was used as supporting electrolyte at 0.2 M. Nitrogen was used for sample deaeration.

Photophysical Properties: Photophysical properties of TMR-S and TMR-Se are compared to those of commercially available tetramethylrosamine (TMR-O, Molecular Probes, Inc.) in Table 1. In MeOH, a 20-nm bathochromic shift for TMR-S and a 30-nm bathochromic shift for TMR-Se in the wavelength of the absorption maximum, $\lambda_{max}$, is observed as the chalcogen atom becomes larger and the oscillator strength of the band decreases as indicated by a decrease in the molar extinction coefficient, $\epsilon$.

TABLE 1

Absorption ($\lambda_{max}$) and Fluorescence ($\lambda_F$) Maxima in MeOH, Quantum Yields for Fluorescence ($\phi_F$) and the Generation of Singlet Oxygen [$\phi(^1O_2)$], Reduction Potentials (E°), and n-Octanol/Water Partition Coefficients (log P) for TMR-O, TMR-S, and TMR-Se.

| Compd | $\lambda_{max}$, nm (log $\epsilon$) | $\lambda_F$, nm[a] | $\phi_F$ ± sd[b] | $\phi(^1O_2)$ ± sd[c] | E°, V[d] | log P[e] |
|---|---|---|---|---|---|---|
| TMR-O | 552 (4.92) | 575 | 0.84 ± 0.01 | 0.08 ± 0.01 | −0.94 | 1.5 |
| TMR-S | 571 (4.70) | 599 | 0.44 ± 0.01 | 0.21 ± 0.02 | −0.79 | 1.2 |
| TMR-Se | 582 (4.84) | 608 | 0.009 ± 0.001 | 0.87 ± 0.01 | −0.77 | 1.1 |

[a]Excitation at 532 nm.
[b]Quantum efficiencies using rhodamine 6G as a standard.
[c]Direct detection of singlet-oxygen luminescence using rose bengal as a standard.
[d]In CH$_2$Cl$_2$ with 0.2 N Bu$_4$NBF$_4$ as supporting electrolyte. V vs. the ferrocene/ferrocinium couple (E° = +0.40 V).
[e]pH-6 phosphate buffer as the aqueous phase.

Results

A 25- to 28-nm Stokes shift is observed in the fluorescence emission maximum, $\lambda_F$, which is typical of other cationic dyes. [20] The radiative lifetime, $\tau_{rad}$, decreases from 2.1±0.1 ns in TMR-O to 1.5±0.1 ns for TMR-S to approximately 50 ps for TMR-Se, which is consistent with heavy-atom effects in other cationic dyes. [20]

The rigid nature of the xanthylium core minimizes internal conversion back to the ground state, which leads to dramatic changes in $\phi_F$ and $\phi(^1O_2)$ as the chalcogen atom becomes larger. Fluorescence in TMR-O is highly efficient with $\phi_\Phi$ of 0.84. Intersystem crossing to the triplet, which is necessary for the production of singlet oxygen, is relatively slow with $\phi(^1O_2)$ of 0.08 for TMR-O. As the chalcogen atom becomes larger, the spin-orbit (heavy-atom) effects promote triplet formation relative to fluorescence and $\phi(^1O_2)$ decreases to 0.44 and 0.009 for TMR-S and TMR-Se, respectively, while values of $\phi(^1O_2)$ increase to 0.21 and 0.87 for TMR-S and TMR-Se, respectively.

Chemical Properties: Mitochondrial reduction of a cationic photosensitizer can bleach the photosensitizer, thus limiting it's useful lifetime. Furthermore, the cationic photosensitizer's role as an electron acceptor might impact the redox cascade in mitochondrial respiration. The reduction potentials of TMR-O, TMR-S, and TMR-Se were determined by cyclic voltammetry and values of E° for the cation/neutral radical couple [vs. the ferrocene/ferrocinium couple (Fc/Fc$^+$) at +0.40 V] are compiled in Table 1. An anodic (positive) shift in E° is observed as the chalcogen atom becomes heavier. The reduction of the tetramethylrosamines is more cathodic (more difficult to reduce) than the thiopyrylium dye AA1 [E° of −0.71 V (vs. Fc/Fc$^+$)], which shows antitumor activity by targeting the mitochondria of carcinoma cells [21] and inhibiting mitochondrial ATPase activity. [21]

Example 8

This example demonstrates that the compounds of the present invention can be used for PACT.

Preparation of Oxygenated Red Blood Cells: Packed RBCs were prepared from units of whole blood (500±50 mL) collected in 70 mL CDP in triple-pack container systems (PL146 primary container, Baxter Healthcare, Deerfield, Ill.) by the Research Blood Department, Holland Laboratory for the Biomedical Sciences. Units were centrifuged at 1471×g for 4 minutes and platelet-rich plasma and buffy coat were removed. The packed RBCs were diluted to an hematocrit of approximately 50% with Erythrosol (ref 29), subsequently white cell reduced by using a filter (Leukotrap-SC RC, Pall Medical, East Hill, N.Y.), and oxygenated by adding 230 mL of a 60 to 40 percent $O_2$ to $N_2$ gas mixture to 150 mL of a RBC suspension in a 600 mL container (PL146 plastic, Baxter Healthcare) and by subsequent incubation for 30 minutes at 1 to 6° C. with agitation (orbital shaker, 100 r.p.m., 19-mm orbit, VWR Scientific, West Chester, Pa.). Oxygen levels were measured by use of a blood gas analyzer (Rapidlab 348, Bayer Corp., Medfield Mass.) and were routinely supersaturated with levels greater than 400 mm Hg.

Addition of Virus and Phototreatment: Stock cultures of extracellular and intracellular viruses and Erythrosol were added to oxygenated, white cell reduced, red cells to produce a final hematocrit of 20%. The volume of the pathogen spike represented <10-percent of the total volume of the cell suspension. A volume of 10 mM aqueous stock of TMR-Se or 1 mM RhII-Se was added to 20% hematocrit red cells to yield final dye concentrations of 1 µM or 15 µM, respectively. For experiments conducted with red cell suspensions containing dipyridamole, a volume of 10 mM aqueous stock of the quencher was added to virus containing red cells prior to the addition of dye in order to yield a final concentration of 200 µM. Red cell suspensions containing virus, dye, and, when indicated, dipyridamole were thoroughly mixed and divided into 2 mL aliquots in polystyrene culture dishes (50 mm bottom diameter) to produce a 1 mm blood film. All treated and control samples contained dye but control samples were not illuminated. We incubated samples at room temperature for 15 minutes in the dark prior to illumination.

Because RBC storage studies required greater volumes than virus studies, 21 petri dishes containing 2 mL each of 20-percent hematocrit RBCs with sensitizers and, when indicated, with dipyridamole, were illuminated with agitation on a reciprocal shaker (70 cycles/min, Melco Engineering Corp., Glendale, Calif.), their contents pooled, and transferred to a 150-mL PL145 container to provide sufficient volume for RBC storage studies. RBC suspensions prepared at 20-percent hematocrit that did not contain sensitizer or quencher and were not illuminated served as controls.

Samples were placed on an air-cooled transparent plastic stage and positioned approximately 3 cm between two in-house fabricated light banks that illuminated samples from above and below. Each bank contained eight cool-white fluorescent bulbs (F20T12-CW, General Electric, Circleville, Ohio). For experiments using RhII-Se, light was filtered through amber 2422 plexigas plastic (with a cutoff circa 535 nm) to prevent absorption by dipyridamole, which may, in certain circumstances, behave as a photosensitizer (ref 30). The source produced broadband light at the sample surface of mW/cm$^2$ (without the amber filter) or mW/cm$^2$ (with the amber filter). Fluence rates were measured using a handheld laser power meter with a silicon cell sensor (Edmunds Industrial Optics, Barrington, N.J.).

Mammalian Virus Assays: VSV was provided by Med Lieu (Hyland Diagnostics, Duarte, Calif.). Bovine virus diarrhea virus (BVDV) was purchased from the American Type Culture Collection, Manassas, Va.). Pseudorabies virus (PRV) was provided by Shirley Mieka (American Red Cross, Rockville, Md.).

Extracellular virus assays: VERO (isolated from African green monkey kidney, CCL81, ATCC) and MDBK (CRL6071, ATCC) cells were propagated in medium (RPMI-1640 supplemented with glutamine, Biofluids, Rockville, Md.) supplemented with 10-percent bovine serum. Cells were seeded into six-well culture plates and allowed to grow to confluency. Control and phototreated samples were serially diluted 10-fold, plated onto confluent VERO (for VSV and PRV) or MDBK (for BVDV) cell monolayers, incubated for 30 to 60 minutes, depending on the virus, and gently rocked at 37° C. for virus adsorption to cells. The inoculum was removed by aspiration and washed with PBS, a semi-liquid agar layer (0.2-percent) was added to each well and infected monolayers were incubated at 37° C. in air containing 5-percent $CO_2$. Incubation periods were: VSV, 1 day; PRV, 4 days; BVDV, 5 to 6 days. After incubation, the agar layer was removed by aspiration and the monolayer was stained with 0.1-percent crystal violet in ethanol for at least 15 minutes. The stain was removed by aspiration, the plates were washed with water, and the plaques enumerated.

Intracellular virus assays. Virus-infected cells were prepared by inoculating a confluent VERO monolayer with VSV at a virus-to-cell ratio of >1. The inoculum was incubated for 30 minutes at room temperature to allow entry of the virus and was subsequently removed by aspiration. Infected monolayers were washed with RPMI-1640 and detached from the culture flask by the addition of 0.05% trypsin and 0.02% versene solution 5 minutes. The resulting infected cell suspension was diluted approximately 1 in 15 in RPMI-1640, and infected cells were centrifuged at 200×g for 10 minutes. The infected cell pellet was resuspended in additive solution and subsequently added to white cell-reduced, oxygenated RBCs to give a final Hct of 45%. Control and phototreated RBCs were first diluted 2-fold and then serially diluted 10-fold. The 2-fold dilution was performed to eliminate RBC interference with VSV plaque formation. Infected cells were inoculated onto confluent, uninfected VERO cell monolayers in six-well plates. As in the assay for extracellular virus, semi-liquid agar (0.2%) was added to each well, and the infected monolayers were incubated at 37° C. in air containing 5% $CO_2$ for 1 day. The agar layer was removed by aspiration, and the monolayer was washed with phosphate-buffered saline to remove RBCs and stained by the addition of 0.1% crystal violet in ethanol for at least 15 minutes. After removal of the stain by aspiration, plates were washed with water. Plaques were counted, and they represented viral growth arising from intracellularly infected VERO cells.

Red Cell Assays: Supernatant Hb was determined by the tetramethylbenzidine method. Total hemoglobin was determined by an automated cell counter (Cell Dyn 3700, Abbott Laboratories, Abbott Park, Ill.). Extracellular potassium was measured using a blood gas and electrolyte analyzer (Rapid-Lab 348, Bayer Corp).

TMR-Se was observed to have extremely high extracellular virucidal activity with little apparent hemolysis during storage. Only 1 μM of compound and 2 J $cm^{-2}$ of light were required to inactivate >7.4 $log_{10}$ of extracellular VSV in 20% hematocrit red cells. With 45% hematocrit red cells, >7.4 $log_{10}$ of extracellular VSV was inactivated with 5 μM TMR-Se and 2 J $cm^{-2}$ of light. Under these conditions, there was little hemolysis (0.22 and 0.36% respectively) during 42-day storage. Day 1 potassium release was moderate (10 mM supernatant values) with samples treated at 20 hematocrit and high (45% supernatant values) with samples treated at 45% hematocrit. TMR-Se did not activate intracellular VSV (only 0.5 $log_{10}$ inactivation) under these conditions.

Similar to TMR-Se, TMR-S also could inactivate extracellular virus but required 5 times higher concentrations and more light exposure. More than 8 $log_{10}$ of extracellular VSV was inactivated using 5 μM TMR-S and 7.4 J $cm^{-2}$ light in 20% hematocrit red cells. However, only 1.5 $log_{10}$ of intracellular VSV could be inactivated under more stringent conditions (50 μM and 7.4 J $cm^{-2}$); however, massive and immediate hemolysis (>>1%) was visually observed immediately after phototreatment under these conditions.

With respect to RhII-Se-moderate levels of RhII-Se were required for extracellular and intracellular VSV inactivation. More than 8.5 $log_{10}$ of extracellular and >6.5 $log_{10}$ of intracellular VSV were inactivated using 15 μM RhII-Se and 2.5 J cm-2 light in 20% hematocrit red cells. Under these conditions, there was little hemolysis (0.30%) during 42-day storage. Potassium release in phototreated red cells was low, with 5.5 mM potassium released to the supernatant after 1 day of storage.

The extremely high extracellular and intracellular inactivation levels and low hemolysis during storage with RhII-Se is unexpected. In a study of over 50 photosensitizers, it was observed that none could inactivate virus to this degree without significant hemolysis during storage. A subsequent study investigating the potential of RhII-Se to bind to the red cell membrane suggests that lack of binding to the red cell membrane may be the reason why so little hemolysis is observed following phototreatment.

Example 9

This example suggests that compounds which have an aryl group as a substituent in the 9-position have higher virucidal activity than those with other groups, particularly methyl as substituent in the 9-position. In a comparative experiment, a compound 2 (FIG. 3) was synthesized, which differed from the other derivatives in that the 9-substituent is not an aryl group (methyl in this example). This sample showed reduced virucidal activity in either extracellular (<2.5 $log_{10}$) or intracellular (<0.5 $log_{10}$) testing over a wide range of concentrations.

The following examples describe the ability of the compounds of the present invention (such as TMR-O, TMR-S, and TMR-Se) to be transported by P-glycoprotein (Pgp) into chemo-resistant CR1R12 cells. The results indicate that these compounds can be used as potent photosensitizers for PDT and may simultaneously act as reversal agents of Pgp function.

Experimental: Chemicals and reagents were purchased from Sigma Aldrich Chemical Co. (St. Louis, Mo.) unless otherwise noted. Cell culture media and antibiotics were obtained from Grand Island Biological (Grand Island, N.Y.). Fetal bovine serum (FBS) was purchased from Atlanta Biologicals (Atlanta, Ga.). Tetramethylrosamine and Calcein AM (calcein acetoxymethyl ester) were purchased from Molecular Probes (Eugene, Oreg.). Both TMR-S and TMR-Se were prepared as described herein.

Cells and culture conditions: Cultured cells used in this study were the Chinese hamster ovary parental cell line AUXB1, [47] a chemo-sensitive cell line in which Pgp content is very low and the multidrug resistant cell line CR1R12 which highly constituitively expresses Pgp. Multidrug resistance in CR1R12 cells were established from the $CH^RC5$ cell line [46] by sequential culturing in increasing concentrations of colchicine with 5 μg $mL^{-1}$ being the final concentration used. Cell lines were maintained in passage culture on 60-mm diameter polystyrene dishes (Corning Costar, Corning, N.Y.) in 4.0 mL Minimum Essential Medium (α-MEM) supplemented with 10% fetal bovine serum (FBS), 50 units $mL^{-1}$ penicillin G, 50 ug $ml^{-1}$ streptomycin and 1.0 ug $mL^{-1}$ Fungizone® (complete medium). Only cells from passages 1-10 were used for experiments. A stock of cells, passages 1-4, were maintained at −86° C. to initiate the experimental cultures. Cultures were maintained at 37° C. in a 5% $CO_2$ humidified atmosphere (Forma Scientific, Marietta, Ohio). Passage was accomplished by removing the culture medium, adding a 1.0 mL solution containing 0.25% trypsin, incubating at 37° C. for 2 to 5 minutes to remove cells from the surface followed by seeding new culture dishes with an appropriate number of cells in 4.0 mL of α-MEM. Cell counts were performed using a particle counter (Model ZM, Coulter Electronics, Hialeah, Fla.).

Example 10

Measurement of dye uptake into cell monolayers: Cell lines, AUXB1 or CR1R12, were seeded on 96-well plates in 200 μL/well α-MEM at 1-4×10$^4$ cells/well. Twenty four hours after seeding, verapamil at 7.0×10$^{-6}$ M was added to selected cells in complete medium and cultures were incubated in the dark at 37° C. for 2 h. Dyes were then added to the cultures at 1×10$^{-5}$ M in complete medium. Cells were incubated in the dark for selected times in the presence of each dye with or without verapamil for the time course study and for 2 hr for comparative studies. The medium was then removed and the monolayers washed once with 200 μL 0.9% NaCl and an additional 200 µL 0.9% NaCl was then added. The fluorescence of the intracellular dye was then determined using a multi-well fluorescence plate reader (Gemini, Molecular Devices, Palo Alto, Calif.). The excitation/emission wavelengths were set at 490/570 for TMR-O and 540/600 for TMR-S. Because of the weak fluorescence signal emitted by TMR-Se, we were unable to obtain uptake data for this analogue. Intracellular dye concentration is expressed as fmole/cell.

Example 11

Photoradiation of Cell Cultures: Cell lines, AUXB1 or CR1R12, were seeded on 96-well plates in 200 µL/well α-MEM at $1-4\times10^4$ cells/well. Rhodamine analogues were then added directly to the cell culture medium at various concentrations and incubated for 2 h in the dark as above. The medium was then removed and 200 µL α-MEM minus FBS and phenol red (clear medium) were added to each well. One plate, with the lid removed, was then exposed to 350-750 nm light delivered at 1.4 mW $cm^{-2}$ for 1 h (5.0 J $cm^{-2}$) from a filtered halogen source while a parallel plate was kept in the dark during the irradiation period. Immediately following irradiation the clear medium was replaced with complete medium and the monolayers were incubated for an additional 24-h period. Subsequently, cells were trypsinized and counted using the Coulter counter to determine cell viability. Determination of cell viability by cell counting is performed according to an earlier method. [48] Briefly, cells that detach from the surface of a culture plate stain with trypan blue, i.e. are nonviable, while all cells that remain attached to the surface exclude trypan blue, 100% viable. We were unable to seed new culture plates with cells that detached from the surface after treatment, while cells that remained attached after treatment continued to grow and multiply. Thus, we count only those cells that remain attached to the culture plate surface after treatment and compare those numbers with the cell numbers obtained from control cells, cells not exposed to either dye or light. Data are then expressed as percent cell viability, treated cell counts/control cell counts.

Example 12

Calcein AM uptake: CR1R12 or AUXB1 cells were seeded on 96-well plates in 200 µL/well α-MEM at $1-4\times10^4$ cells/well. Rhodamine analogues at $1.0\times10^{-6}$ M were added to cell cultures on 96-well plates in complete medium for 2 h in the dark at 37° C. The medium containing the dyes was removed and replaced with clear MEM. A plate, with the lid removed, was then exposed to 350-750 nm light delivered at 1.4 mW $cm^{-2}$ for 1 h (5.0 J $cm^{-2}$) from a filtered halogen source. Another plate exposed to the same culture and dye incubation conditions was kept in the dark. Also, in another series of experiments, the Pgp modulators verapamil at $7.0\times10^{-6}$ M or $7.0\times10^{-5}$ M or cyclosporin A at $7.0\times10^{-6}$ M were incubated with the cells in the complete medium for 15 min. Immediately following irradiation or incubation with the modulators, Calcein AM was added to each well at $1.0\times10^{-6}$ M in clear medium. The appearance of a fluorescence signal at 530 nm, excitation 485 nm, was then followed in the plate reader over a 30 min time period. The rate of uptake was calculated from the slope of the line obtained in each experimental protocol and the data are expressed as percent of control Calcein AM uptake, the rate of Calcein AM taken up into cells that were not exposed to TMR analogues or Pgp modulators.

Example 13

Figure 6:
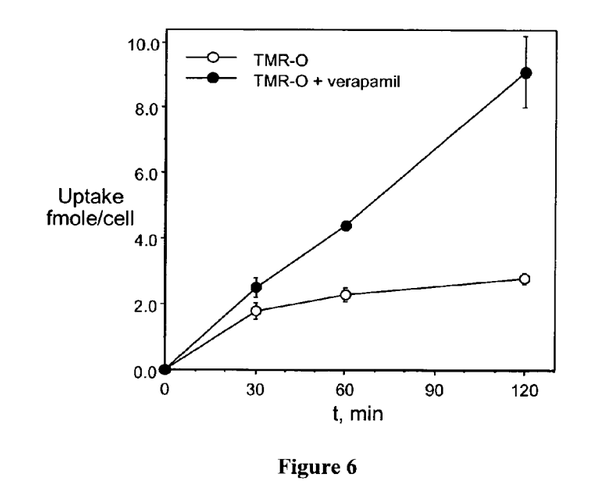
FIG. 6. Time course of the uptake of TMR-O ($1\times10^{-5}$ M) into cultured Pgp-expressing CR1R12 cells in the absence (open circles) or the presence (filled circles) of $7\times10^{-6}$ M verapamil. Experimental conditions are described in detail in the Experimental Section. Each data point, expressed as fmole TMR-O/cell, represents the mean of three separate experiments. Data for each experiment was calculated from results obtained from at least four wells of a 96-well culture plate, bars are the SEM.

Time Course of Uptake of TMR-O into CR1R12 Cells: The development of the fluorescence signal from TMR-O at 570 nm was followed in cultured CR1R12 cells either exposed to $7\times10^{-6}$ M verapamil 2 h prior to dye addition or in cultures without previous exposure to verapamil. The data in FIG. 6 clearly show that verapamil enhances the uptake of TMR-O into CR1R12 cells compared to those cultures not previously exposed to verapamil. The increase in intracellular uptake of TMR-O in the presence of verapamil becomes statistically significant (P<0.005) by 1 h after dye addition to monolayers of cells.

Example 14

Figure 7:
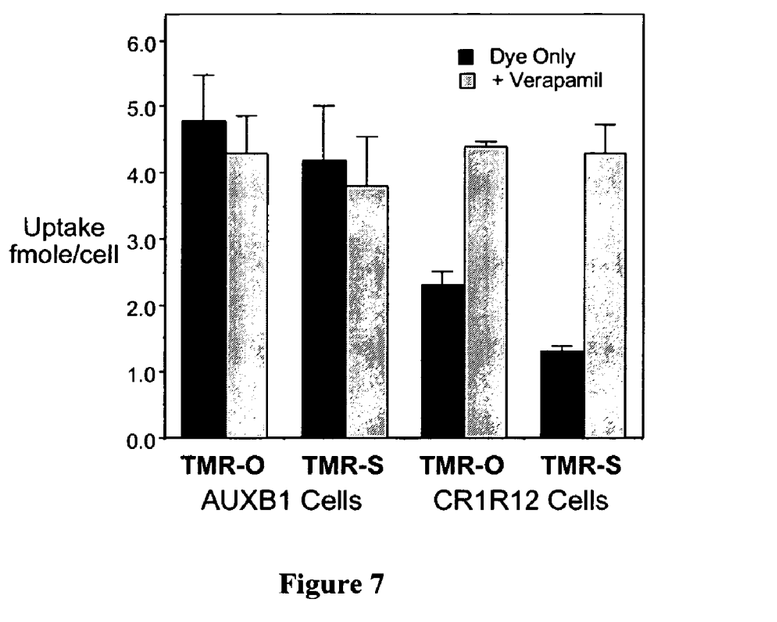
FIG. 7. Comparison of the uptake of $1\times10^{-5}$ M TMR-O or TMR-S after 1 h into cultured, chemo-sensitive AUXB1 and chemo-resistant CR1R12 cells after 1-h incubation in the absence (solid columns) or presence (striped columns) of $7\times10^{-6}$ M verapamil. Experimental conditions are described in detail in the Experimental Section. Each column, expressed as fmole of dye/cell, represents the mean of the data obtained from three separate experiments. Data for each experiment was calculated from results obtained from at least four wells of a 96-well culture plate, bars are the SEM.

Comparison of TMR-O and TMR-S uptake into AUXB-1 or CR1R12 cells: TMR-O or TMR-S was added for 1 h at $1\times10^{-5}$ M to cultured AUXB-1 or CR1R12 cells, either alone or after cells had been incubated with $7\times10^{-6}$ M verapamil for 2 h as above. The data in FIG. 7 demonstrate that the intracellular accumulation of either TMR-O or TMR-S was similar in AUXB1 cells in the absence or the presence of verapamil. In CR1R12 cells, the accumulation of both TMR-O and TMR-S was significantly enhanced in the presence of verapamil compared to cells not previously exposed to verapamil. A more than 3-fold increase in uptake for TMR-S was obtained. The uptake of TMR-S in the chemo-resistant cell line, CR1R12, in the presence of verapamil was equivalent to its uptake in the chemo-sensitive parent cell line AUXB1 in the absence or presence of verapamil. In AUXB1 cells in the absence or presence of verapamil and in CR1R12 cells in the presence of verapamil, the uptake of TMR-O was equivalent to the uptake of TMR-S. These data clearly show that verapamil, a strong modulator of Pgp function, significantly effects the uptake of TMR-O or TMR-S in the chemo-resistant cell line CR1R12 while no effect was seen in the chemo-sensitive AUXB1 cell line. Under the conditions employed, the results strongly suggest that TMR-S is a transport substrate for Pgp, similar to TMR-O.

Example 15

Figure 8:
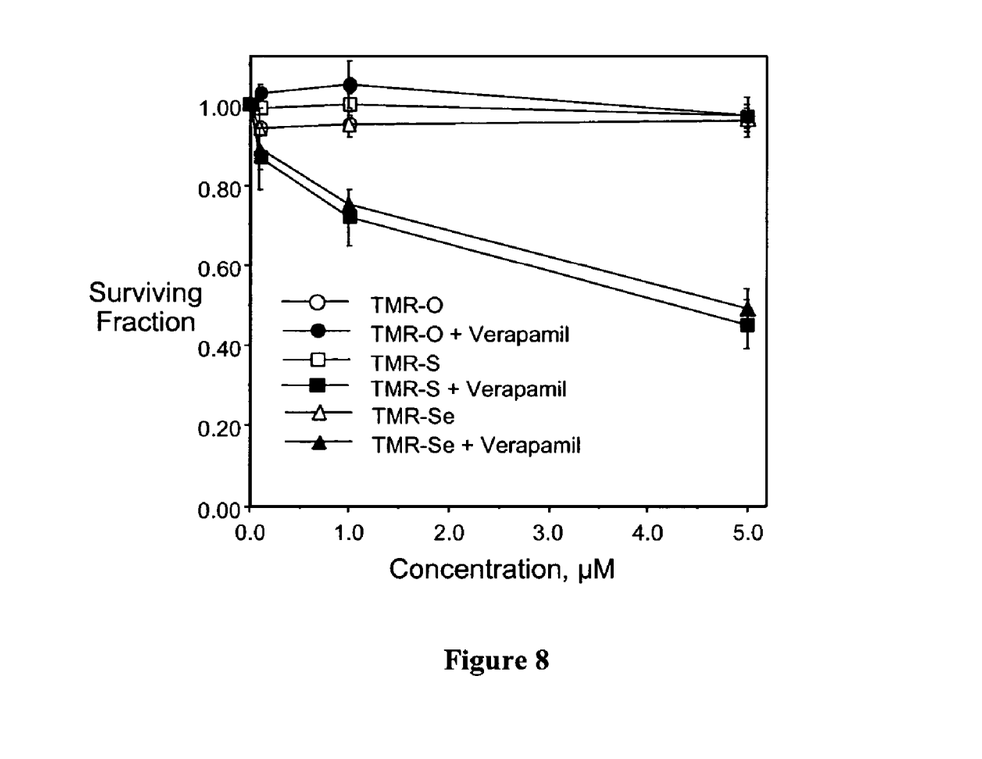
FIG. 8. Cell viability of cultured chemo-resistant CR1R12 cells 24 h after a 2-h incubation with (filled symbol) or without (open symbol) $7\times10^{-6}$ M verapamil followed by a 2-h incubation with TMR-O (circles), TMR-S (squares) or TMR-Se (triangles) at indicated concentrations (x-axis) and 1-h exposure of the culture plates to light. Experimental and light exposure conditions are described in detail in the Experimental Section. Each data point represents the mean, expressed as percent of control cell viability (cells not exposed to verapamil, dyes or light) of at least three separate experiments performed in triplicate, error bars are the SEM. Cells exposed to light alone or dyes alone in the dark using the same conditions showed no significant loss in cell viability.

Phototoxicity toward CR1R12 chemo-resistant cells: The data in FIG. 8 depict the results obtained when CR1R12 cells are exposed to TMR analogues and 5.0 J $cm^{-2}$ light with or without $7\times10^{-6}$ verapamil. The data clearly demonstrate that none of the TMR analogues are effective as photosensitizers of CR1R12 cells in the absence of previous exposure to verapamil. However, when TMR-S and TMR-Se were added to CR1R12 cells after verapamil exposure for 2 h, irradiation of cultures with broad band white light caused significant cytotoxicity. TMR-O showed no significant phototoxicity in the absence or presence of verapamil even at the highest concentration, presumably due to its relatively low singlet oxygen production. [19] These data show that TMR-S and TMR-Se are phototoxic to chemo-resistant CR1R12 cells when a Pgp modulator is present indicating that uptake ensues and that the dyes are able to reach and cause damage to a critical intracellular sites during irradiation.

Example 16

Figure 9:
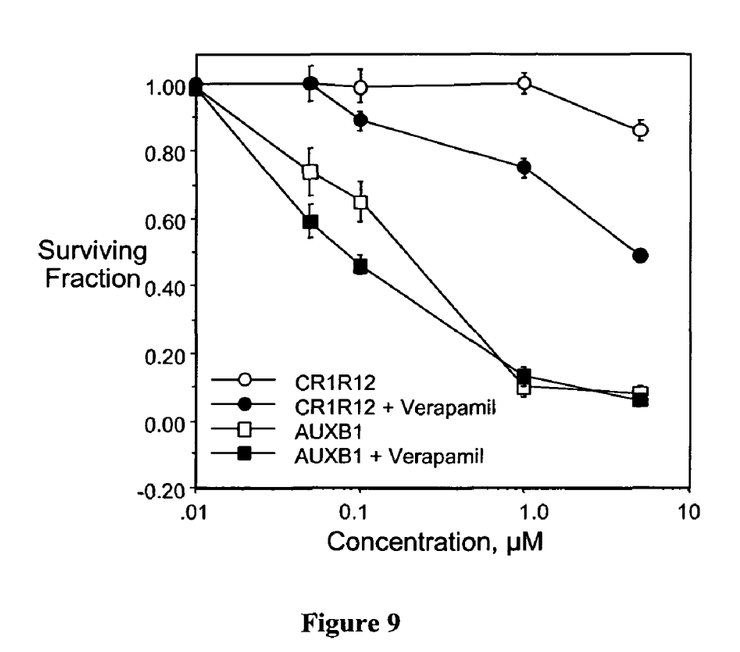
FIG. 9. Comparison of the effects of TMR-Se and light exposure on the cell viability of cultured chemo-resistant CR1R12 cells (circles) or chemo-sensitive AUXB1 cells (squares) or in the absence (empty symbol) or presence (filled symbol) of $7\times10^{-6}$ M verapamil. Experimental and light exposure conditions are described in detail in the Experimental Section. Each data point represents the mean, expressed as percent of control cell viability (cells not exposed to verapamil, dye or light) of at least three separate experiments performed in triplicate, error bars are the SEM. Cells exposed to light alone or dye alone in the dark using the same conditions showed no significant loss in cell viability.

Comparison of TMR-Se phototoxicity towards AUXB1 or CR1R12 cells: For comparison studies, parallel phototoxicity experiments were performed both with AUXB1 cells, which have low levels of Pgp, and with CR1R12 cells, which constituitively express high levels of Pgp. The data displayed in FIG. 9 demonstrate that the chemo-sensitive AUXB1 cells are equally susceptible to phototoxicity using TMR-Se with or without previous exposure to $7\times10^{-6}$ M verapamil while significant phototoxicity towards CR1R12 cells only occurs when verapamil is present.

Example 17

Effect of TMR-S or Se photosensitization on the intracellular uptake of Calcein AM: Calcein AM (CAM) is a non-fluorescent, hydrophobic compound that readily crosses the plasma membrane of normal cells. Once inside the cell, the ester bonds of CAM are enzymatically cleaved transforming it into the highly fluorescent, hydrophilic calcein. Appearance of the calcein fluorescence signal following exposure of cells to CAM indicates the intracellular uptake of CAM followed by ester hydrolysis to form calcein and retention of calcein in the cytosol of the cell.

Figure 10:
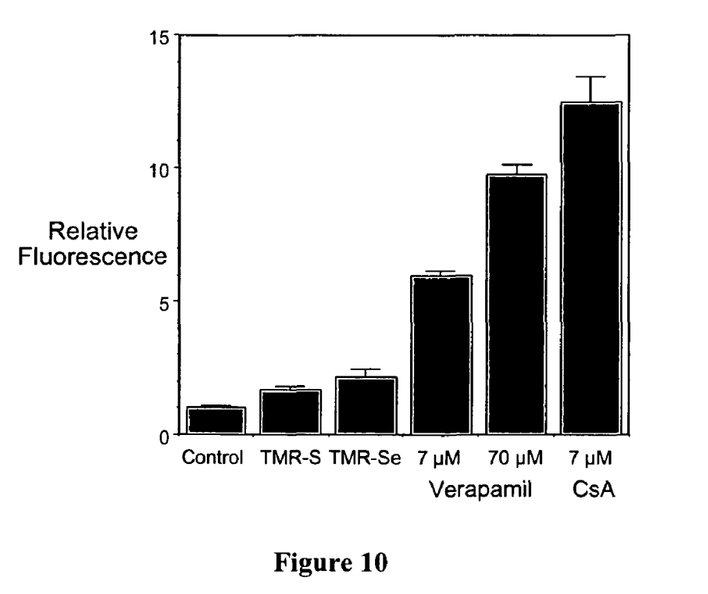
FIG. 10. Uptake of Calcein AM (CAM) into cultured chemo-resistant CR1R12 cells after exposure to the Pgp modulators verapamil ($7\times10^{-6}$ M or $7\times10^{-5}$ M) or cyclosporin A ($7\times10^{-6}$ M) or after cells were exposed to TMR-S or TMR-Se ($1\times10^{-5}$ M) for 2 h in the dark followed by 5.0 J cm$^{-2}$ irradiation. Experimental and light exposure conditions are described in detail in the Experimental Section. Uptake of CAM is measured over a 30-min time period and is expressed as the relative rate of uptake measured in control cells (cells not exposed to verapamil, CsA, dyes or light, relative rate of 1.00±0.03). Each column represents the mean of at least three separate determinations, bars are the SEM.

Cells were exposed to TMR-S or TMR-Se ($1\times10^{-5}$ M) with or without light exposure or to the Pgp modulators verapamil or cyclosporin A (CsA) in the dark. Following exposure to the dyes with or without light or to the modulators, CAM was added at $1\times10^{-6}$ M and its intracellular accumulation over 30 min was monitored by measuring the increase in calcein fluorescence at 530 nm with excitation at 485 nm. The data displayed in FIG. 10 show that the Pgp modulators verapamil and CsA increased the uptake of CAM into CR1R12 cells from 6 to 13 fold over control CAM uptake in the absence of any modulators. Exposure of CR1R12 cells to TMR-S or TMR-Se for 2 h in the dark resulted in no significant change in the intracellular accumulation of CAM (data not shown). However, 1 h of light exposure after incubation of cells with TMR-S or TMR-Se resulted in an up to 2-fold increase in CAM uptake.

Parallel experiments were performed with the parent cell line, AUXB1. In these chemo-sensitive cells, CAM in the presence of Pgp modulators was accumulated intracellularly at a rate equivalent to that obtained for control AUXB1 cells, 1000±30 relative fluorescence units (RFU) of calcein/min/1× $10^5$ cells. This rate of CAM uptake into AUXB1 cells was 10-fold greater than that measured in control CR1R12 cells at 94±3 RFU/min/1×$10^5$ cells. Curiously, higher concentrations of TMR-S or TMR-Se plus light exposure virtually abolished CAM uptake into AUXB1 cells. This result could be due to factors such as damage to the plasma membrane system(s) responsible for intracellular accumulation of CAM or inhibition of intracellular esterases responsible for cleaving the ester bond on CAM that provides a fluorescent compound. These data, taken together, demonstrate that TMR-S and TMR-Se and light, under the conditions employed, do increase the intracellular accumulation of the Pgp substrate CAM into chemo-resistant CR1R12 cells. The experimental conditions remain to be optimized but these initial experiments demonstrate that highly expressing Pgp cells can be altered by these tetramethylrosamine analogues to take in 2 times more Pgp substrate than cells not exposed to the dyes and light.

REFERENCES (1) Peterson, O. G.; Tuccio, S. A.; Snavely, B. B. *Appl. Phys. Lett.* 1970, 17, 245.
(2) Ali, M.; Moghaddasi J.; Ahmed, S. A. *J. Appl. Optics.* 1990, 29, 3945.
(3) Karstens, T.; Kobs, K. *J. Phys. Chem.* 1980, 84, 1871.
(4) Preininger, C.; Mohr, G. J.; Klimant I.; Wolfbeis, O. S. *Anal. Chim. Acta* 1996, 334, 113.
(5) Liu, J.; Diwu, Z.; Leung, W.-Y.; Lu, Y.; Patch, B.; Haugland, R. P. *Tetrahedron Lett.* 2003, 44, 43555.
(6) Johnson, L. V.; Walsh, M. L.; Bockus, B. J.; Chen, L. B. *J. Cell Biol.* 1981, 88, 526.
(7) Shea, C. R.; Sherwood, M. E.; Flotte, T. J.; Chen, N.; Scholz, M.; Hasan, T. *Cancer Res.* 1990, 50, 4167.
(8) Summerhayes, I. C.; Lampidis, T. J.; Bernal, S. D.; Nadakavukaren, J. J.; Nadakavukaren, K. K.; Shepard, E. L.; Chen, L. B. *Proc. Natl. Acad. Sci. U.S.A.* 1982, 79, 5292.
(9) Davis, S.; Weiss, M. J.; Wong, J. R.; Lampidis, T. J.; Chen, L. B. *J. Biol. Chem.* 1985, 260, 13844.
(10) Lampidis, T. J.; Bernal, S. D.; Summerhayes, I. C.; Chen, L. B. *Ann. N.Y. Acad. Sci.* 1982, 395, 299.
(11) Bernal, S. D.; Lampidis, T. J.; McIsaac, R. M.; Chen, L. B. *Science* 1986, 222, 169.
(12) Dougherty, T. J.; Gomer, C. J.; Henderson, B. W.; Jori, G.; Kessel, D.; Korbelik, M.; Moan, J.; Peng, Q. *J. Natl. Cancer Inst.* 1998, 90, 889.
(13) Shea, C. R.; Chen, N.; Wimberly, J.; Hasan, T. *Cancer Res.* 1989, 49, 3961.
(14) Menzel, R.; Thiel, E. *Chem. Phys. Lett.* 1998, 291, 237.
(15) Kessel, D.; Woodburn, K. *Br. J. Cancer* 1995, 71, 306-310.
(16) Pal, P;, Zeng, H.; Durocher, G.; Girard, D.; Li, T. C.; Gupta, A. K.; Giasson, R., Blanchard, L;, Gaboury, L.; Balassy, A.; Turmel, C.; Laperriere, A.; Villeneuve, L. *Photochem. Photobiol.* 1996, 63, 161.
(17) Villeneuve, L.; Pal, P.; Durocher, G.; Migneault, D.; Girard, D.; Giasson, R.; Balassy, A.; Blanchard, L.; Gaboury, L. *J. Fluorescence* 1996, 6, 209.
(18) Stracke, F.; Ma. Heupel, Ma. Thiel, E. *J. Photochem. Photobiol. A.* 1999, 126, 51.
(19) Brennan, N. K.; Donnelly, D. J., Detty, M. R. *J. Org. Chem.* 2003, 68, 3344.
(20) Detty, M. R.; Merkel, P. B. *J. Amer. Chem. Soc.* 1990, 112, 3845.
(21) Sun, X.; Wong, J. R.; Song, K.; Hu, J.; Garlid, K. D.; Chen, L. B. *Cancer Res.* 1994, 54, 1465.
(22) Brennan, N. K.; Hall, J. P.; Davies, S. R.; Gollnick, S. O.; Oseroff, A. R.; Gibson, S. L.; Hilf, R.; Detty, M. R. *J. Med. Chem.* 2002, 45, 5123.
(23) You, Y.; Ahsan, K.; Detty, M. R. *J. Am. Chem. Soc.* 2003, 125, 4918.
(24) Pandey, R. K.; Sumlin, A. B.; Constantine, S.; Aoudia, M.; Potter, W. R.; Bellnier, D. A.; Henderson, B. W.; Rodgers, M. A.; Smith, K. M.; Dougherty, T. J. *Photochem. Photobiol.* 1996, 64, 194.
(25) Baker, G. A.; Bright, F. V.; Detty, M. R.; Pandey, S.; Stilts, C. E.; Yao, H. R. *J. Porphyrins Phthalocyanines* 2000, 4, 669.
(26) Gottesman, M. M.; Fojo, T.; Bates, S. *Nature Reviews/Cancer* 2002, 2, 48.
(27) Vasey, P. A. *Brit. J. Cancer* 2003, 89, Suppl. 3, 523.
(28) Lehnert, M. *Euro. J. Cancer* 1996, 32A, 912.
(29) Baldini, N.; Scotlandi, K.; Barbanti-Brodano, G.; Manara, M. C.; Maurici, D.; Bacci, G.; Bertoni, F.; Picci, P.; Sottilis, S.; Campanacci, M; Serra, M. *New Eng. J Med.* 1995, 333, 1380.
(30) Lehnert, M.; Mross, K.; Schueller, J.; Thuerlimann, B.; Kroeger, N.; Kupper, H. *Brit. J Cancer* 1998, 77, 1155.
(31) Burger, H.; Foekens, J. A.; Look, M. P.; Meijer-van Gelder, M. E.; Klijn, J. G. M.; Wiemer, E. A. C.; Stoter, G.; Nooter, K. *Clin. Cancer Res.* 2003, 9, 827.
(32) Scotto, K. W. *Oncogene* 2003, 22, 7496.
(33) Baker, E. K; El-Osta, A. *Exp. Cell Res.* 2003, 290, 177.
(34) Tiberghien, F.; Loor, F. *Anti-Cancer Drugs* 1996, 7, 568.
(35) Hirsch-Ernst, K. I.; Ziemann, C.; Rustenbeck, I.; Kahl, G. F. *Toxicology* 2001, 167, 47.

(36) Loor, F.; Tiberghien, F.; Wenandy, T.; Didier, A.; Traber, R. *J. Med. Chem.* 2002, 45, 4598.
(37) Fisher, G. A.; Lum, B. L.; Hausdorff, J.; Sikic, B. I. *Euro. J. Cancer* 1996, 32A, 1082.
(38) Fojo, T.; Bates, S. *Oncogene* 2003, 22, 7512.
(39) Kessel, D. *Cancer Commun.* 1989, 1, 145.
(40) Eytan, G. D.; Regev, R.; Oren, G.; Hurwitz, C. D.; Assaraf, Y. G. *Euro. J. Biochem.* 1997, 248, 104.
(41) Loetchutinat, C.; Saengkhae, C.; Marbeuf-Gueye, C.; Garnier-Suillerot, A. *Euro. J Biochem.* 2003, 270, 476.
(42) Robey, R.; Bakke, S.; Stein, W.; Meadows, B.; Litman, T.; Patil, S.; Smith, T.; Fojo, T.; Bates, S. *Blood* 1999, 93, 306.
(43) Shapiro, A. B.; Ling, V. *Euro. J. Biochem.* 1998, 254, 189.
(44) Detty, M. R.; Prasad, P. N.; Donnelly, D. J.; Ohulchanskyy, Gibson, S. L.; Hilf, R. *Bioorg. Med. Chem.* 2004, 12, 2537.
(45) Al-Shawi, M. K.; Senior, A. E. *J. Biol. Chem.* 1993, 268, 4197.
(46) Ling, V.; Thompson, L. H. *J Cell Physiol.* 1974, 83, 103.
(47) McBurney, M. W.; Whitmore, G. F. *Cell* 1974, 2, 173.
(48) Gibson, S. L.; Al-Shawi, M. K.; Senior, A. E.; Hilf, R. *Photochem. Photobiol.* 1995, 61, 390.

We claim:
1. A compound having the structure of Formula I:

Formula I wherein E is Se and A⁻ is an anionic group selected from the group consisting of halides, sulfonates; carboxylates; hexafluorophosphate, and tetrafluoroborate; and I)
  i) W, X, Y, and Z are hydrogen;
  ii) $R_1'$, $R_2'$, $R_1''$ and $R_2''$ are independently hydrogen or $C_1$ through $C_8$ branched or unbranched alkyl, and, optionally,
    1) $R_1'$ and $R_2'$ are alkyl groups connected such that they comprise a 3-, 4-, 5-, 6- or 7-membered ring which, optionally, bears alkyl or aryl substituents;
and/or
    2) $R_1''$ and $R_2''$ are alkyl groups connected such that they comprise a 3-, 4-, 5-, 6- or 7-membered ring which, optionally, bears alkyl or aryl substituents;

iii) R is a $C_1$ through $C_8$ alkyl, aryl, heteroaryl, substituted aryl or substituted heteroaryl group;
or
II)
  i) W, X, Y and Z are independently hydrogen or $C_1$ through $C_8$ alkyl;
  ii) $R_1'$, $R_2'$, $R_1''$ and $R_2''$ are independently hydrogen or $C_1$ through $C_8$ alkyl, and wherein $R_1'$ and Y are connected such that they comprise a five, six or seven-membered ring and/or $R_2'$ and Z are connected such that they comprise a five-, six- or seven-membered ring and/or $R_1''$ and W are connected such that they comprise a five-, six- or seven-membered ring and/or $R_2''$ and X are connected such that they comprise a five-, six- or seven-membered ring:

and
iii) R is a $C_1$ through $C_8$ alkyl, aryl, substituted aryl, heterocyclic or substituted heterocyclic group.

2. A compound as claim 1 wherein R is an aryl group which is mono-, di-, or tri-substituted with one or more of the following substituents: —CO₂Me, —CO₂H, dialkylamino groups having alkyl groups which are independently $C_1$ through $C_8$; $C_1$ through $C_8$ alkyl, $C_1$ through $C_8$ alkoxy, and heterocyclic groups.

3. A compound as claim 1 wherein R is an aryl group which is mono-, di-, or tri-substituted with one or more substituents selected from the group consisting of —NMe₂, —NHEt, —NH₂, —Me, —OMe, 1,3-oxazole, 1,3-diazole, 4,5-dihydro-1,3-oxazole, and 4,5-dihydro-1,3-thiazole.

4. A compound as in claim 1 wherein A⁻ is an anionic group selected from the group consisting of Cl, tosylate; and acetate.

5. A compound as in claim 1 wherein $R_1'$, $R_2'$, $R_1''$, and $R_2''$ are methyl.

6. A compound as claim 1 wherein $R_1'$, $R_2'$, $R_1''$, or $R_2''$ is an ethyl, dimethylamino or ethylamino group.

7. A compound as in claim 5, wherein R is an aryl group which bears a heterocyclic substituent at position 2.

8. A compound of claim 1 wherein $R_1'$, $R_2'$, $R_1''$, and $R_2''$ are methyl, and R is $NMe_2$, $NH_2$, Me, ortho-benzoic acid, ortho-methoxybenzoate, ortho-2-amino-2-methylpropyl ester and 2,4,6-trimethylphenyl.

9. A compound of claim 8 wherein $A^-$ is chloride or hexafluorophosphate.

* * * * *